United States Patent
Su et al.

(10) Patent No.: US 8,822,723 B2
(45) Date of Patent: Sep. 2, 2014

(54) PROCESSES OF SYNTHESIZING MULTI-FUNCTIONAL PHOSPHORUS-CONTAINING EPOXY CURING AGENT

(75) Inventors: Wen-Chiung Su, Taoyuan County (TW); Ching-Hsuan Lin, Taichung (TW); Hung-Tse Lin, Taichung (TW)

(73) Assignee: Chung-Shan Institute of Science and Technology, Armaments, Bureau, Ministry of National Defense, Taoyuan County (TW)

( * ) Notice: Subject to any disclaimer, the term of this patent is extended or adjusted under 35 U.S.C. 154(b) by 739 days.

(21) Appl. No.: 13/103,046

(22) Filed: May 7, 2011

(65) Prior Publication Data

US 2012/0130126 A1   May 24, 2012

(30) Foreign Application Priority Data

Nov. 19, 2010   (TW) .............................. 99139886 A

(51) Int. Cl.
*C07F 9/28* (2006.01)
*C07F 9/02* (2006.01)
*C07F 9/6571* (2006.01)

(52) U.S. Cl.
CPC ....... *C07F 9/657172* (2013.01); *C07F 9/65719* (2013.01)
USPC ............................... 564/16; 568/12

(58) Field of Classification Search
CPC ...................................... C07F 9/65685
USPC .............................. 564/16; 568/12
See application file for complete search history.

(56) References Cited

PUBLICATIONS

Ying Ling Liu, Journal of Polymer Science: Part A: Polymer Chemistry, vol. 40, 359-368 (2002).*

* cited by examiner

*Primary Examiner* — Sudhakar Katakam
*Assistant Examiner* — Kofi Adzamli
(74) *Attorney, Agent, or Firm* — Jackson IPG PLLC

(57) ABSTRACT

A series of curing agents are provided. The curing agents are multi-functional and phosphorus-containing. The curing agents have excellent processability to be used as an epoxy resin curing agent. The curing agents can be cured to obtain a phosphorus-containing epoxy thermoset with flame retardancy characteristic. The epoxy thermosets are very fit for circuit board substrate having high glass transition temperature; semiconductor packaging material; and related materials.

18 Claims, 2 Drawing Sheets

Figure 1:
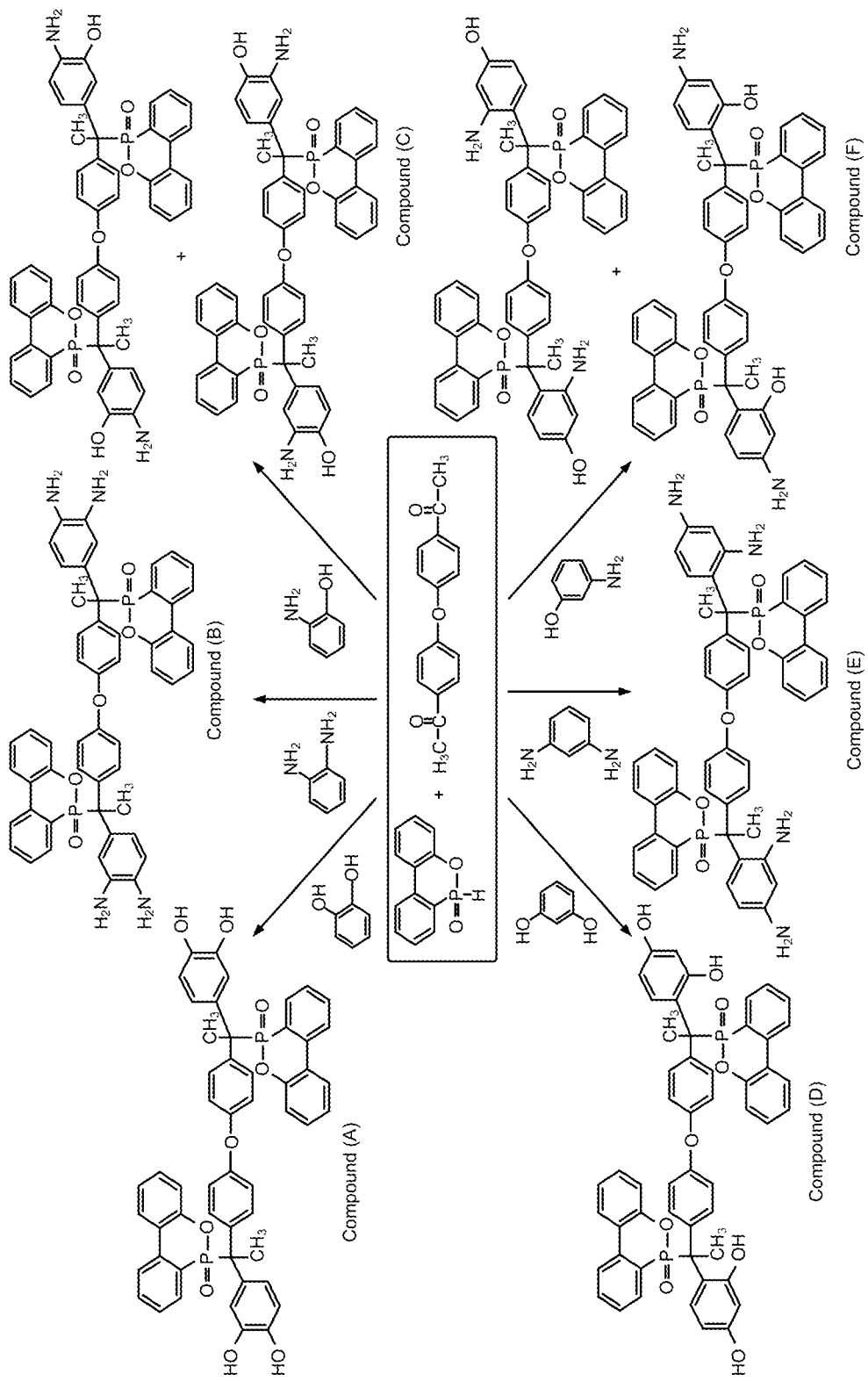

| Sample ID epoxy/curing agent | Phosphorous content % | Nitrogen content % | Tg (°C) | UL-94 grade |
|---|---|---|---|---|
| DGEBA/DDS | 0 | 2.80 | 232 | Burning |
| DAS-1.0 | 1.0 | 2.06 | 214 | V-0 |
| DAS-1.5 | 1.5 | 1.69 | 210 | V-0 |
| DAS-2.0 | 2.0 | 1.33 | 204 | V-0 |
| DBS-1.0 | 1.0 | 2.63 | 224 | V-0 |
| DBS-1.5 | 1.5 | 2.55 | 220 | V-0 |
| DBS-2.0 | 2.0 | 2.46 | 218 | V-0 |
| DCS-1.0 | 1.0 | 2.34 | 219 | V-0 |
| DCS-1.5 | 1.5 | 2.12 | 216 | V-0 |
| DCS-2.0 | 2.0 | 1.89 | 214 | V-0 |

FIG.2

PROCESSES OF SYNTHESIZING MULTI-FUNCTIONAL PHOSPHORUS-CONTAINING EPOXY CURING AGENT

CROSS-REFERENCE TO RELATED APPLICATIONS

None.

TECHNICAL FIELD OF THE DISCLOSURE

The present disclosure relates to a curing agent; more particularly, relates to obtaining cheap materials to fabricate a multi-functional phosphorous compound having good processability to be used as an epoxy resin curing agent.

DESCRIPTION OF THE RELATED ARTS

In an epoxy resin used for print circuit board (PCB), halogen and antimony trioxide are main flame retardants. For example, halogen-containing tetrabromobisphenol-A is a widely used epoxy resin retardant. Yet, those epoxy resin using the halogenated retardant would generate corrosion gas on burning, where carcinogens like doxin or benzofuran may even be generated. Hence, halogen is replaced with phosphorous for fabricating a retardant without halogen.

After 1970, a phosphorous-containing organic compound of 9,10-dihydro-9-oxa-10-phosphaphenanthrene 10-oxide (DOPO) and its derivatives have been used as precursors for reactive flame retardants. In 2001, Y. L. Liu used DOPO to fabricate a phenol type phosphorus epoxy hardener (Y. L. Liu, polymer 2001, 42, 3445-3454), which has the following structure:

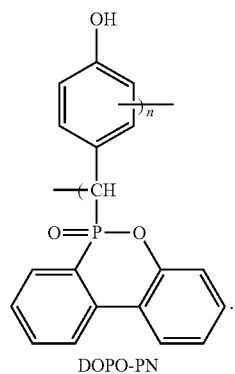

DOPO-PN

In 2002, Y. L. Liu used DOPO to fabricate epoxy resin curing agents containing more phosphorous (Y. L. Liu, J. Polym. Sci. Part A: Polym. Chem. 2002, 40, 359-368; and, Y. L. Liu, et al., polymer 2002, 43, 1773-1779), which have the following structures:

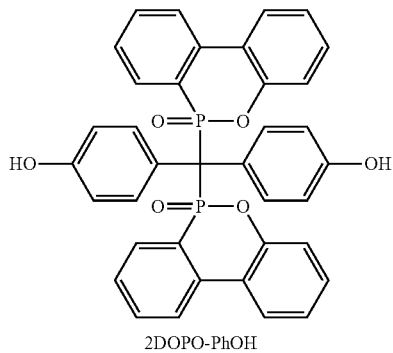

2DOPO-PhOH

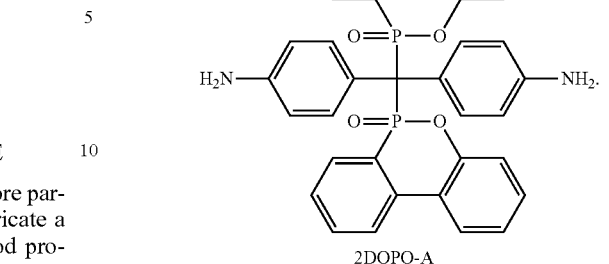

2DOPO-A

In 2007, C. H. Lin et al. used DOPO to fabricate epoxy resin curing agents (C. H. Lin et al., Macromol. chem. phys. 2007, 208, 2628-2641), which have the following structures:

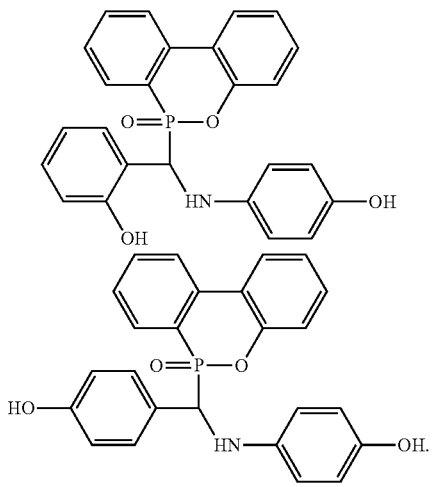

The above epoxy resin curing agents have more and more phosphorous and the products obtained after curing epoxy resin have higher char yields, limited oxygen indexes (LOI) and UL-94 flame retardant grades. However, they have few reactive functional groups and bad spatial structures, so the glass transition temperatures (Tg) of their cured products are not improved.

Therefore, in 2005, C. H. Lin et al. used DOPO and para-rosaniline chloride to fabricate dopo-ta having six functions (C. H. Lin et al., J. Polym. Sci. Part A: Polym. Chem. 2005, 43, 5971-5986), which has more functional groups and enhanced Tg and thermo-stability for its cured product and has the following structure:

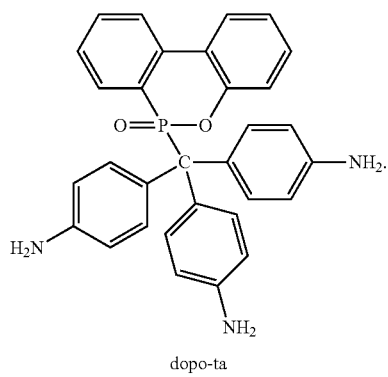 [SMILES: Nc1ccc(C(c2ccc(N)cc2)(c2ccc(N)cc2)P2(=O)Oc3ccccc3-c3ccccc32)cc1]

dopo-ta

Besides, in 2008, Döring fabricates a curing agent (Döring, et al., Macromol. Mater. Eng. 2008, 293, 503-514; and, Dör- ing, et al., European Polymer Journal 2008, 44, 704-715), which is an epoxy resin curing agent having good thermostability and retardancy characteristic and has the following structure:

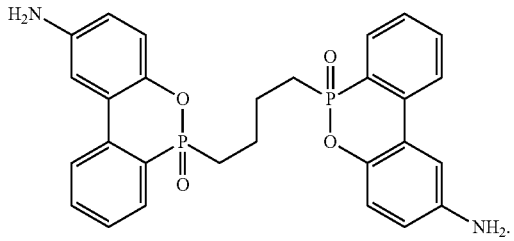 [SMILES: Nc1ccc2c(c1)-c1ccccc1P(=O)(CCCCP1(=O)Oc3ccc(N)cc3-c3ccccc31)O2]

However, the above epoxy resin curing agents all use expensive materials, or, require complex fabrication procedure or expensive catalysts. Thus, they are not economic for industrial use.

In 2005 and 2008, C. H. Lin et al. used (DOPO and rosolic acid) or (4,4'-dihydroxy benzophenone (DHBP) and roiltriol) to fabricate a curing agent having three functions (C. H. Lin et al., J. Polym. Sci. Part A: Polym. Chem. 2005, 43, 2862-2873; and, C. H. Lin et al., J. Polym. Sci. Part A: Polym. Chem. 2008, 46, 7898-7912), which has the following structure:

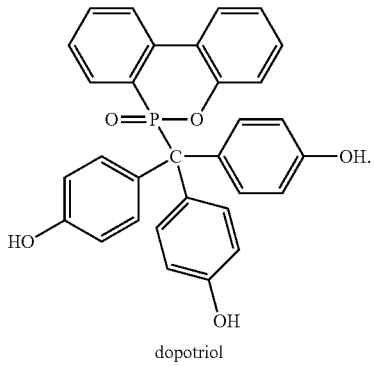 [SMILES: O=P1(C(c2ccc(O)cc2)(c2ccc(O)cc2)c2ccc(O)cc2)Oc2ccccc2-c2ccccc21]

dopotriol

The above epoxy resin curing agents using dopotriol may obtain good Tg and retardancy characteristic. But, the materials used, no matter rosolic acid or DHBP, are expensive and not economic for industrial use. Besides, the curing agents have high melting points and bad solubility, which makes their fabrication costs too high and their industrial uses limited. Hence, the prior arts do not fulfill all users' requests on actual use.

SUMMARY OF THE DISCLOSURE

The main purpose of the present disclosure is to obtain cheap materials to fabricate a multi-functional phosphorous compound having good processability to be used as an epoxy resin curing agent.

The second purpose of the present disclosure is to make use of the curing agent to be fit for high Tg circuit board substrate, semiconductor packaging material and related materials.

To achieve the above purposes, the present disclosure is a process of synthesizing multi-functional phosphorus-containing epoxy curing agents, where the curing agents are a phosphorus compound or a phosphorus mixture; the curing agent has the following formula:

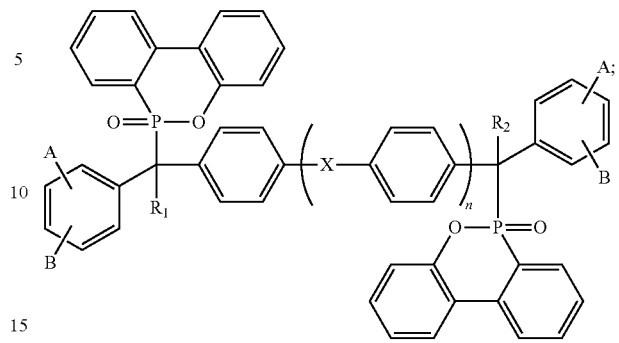

$R_1$ and $R_2$ are $C_1 \sim C_6$ alkane, $C_3 \sim C_6$ alkanecycloalkane group, phenyl group or —$CF_3$; n is an integer selected from 0 to 10; A and B are —OH or —$NH_2$; X is a chemical group selected from null,

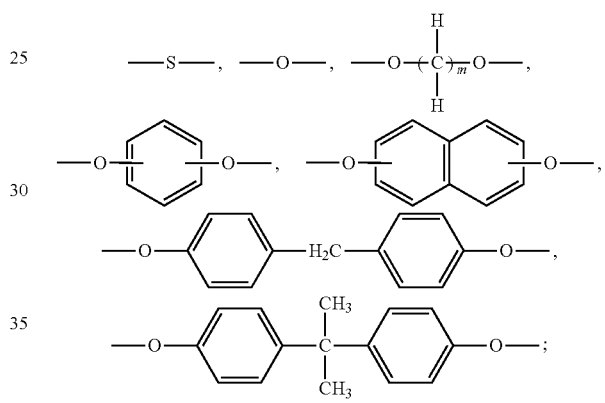

and m is an integer selected from 1 to 10. Accordingly, a novel multi-functional phosphorus-containing epoxy curing agent is obtained.

BRIEF DESCRIPTIONS OF THE DRAWINGS

The present disclosure will be better understood from the following detailed description of the preferred embodiment according to the present disclosure, taken in conjunction with the accompanying drawings, in which FIG. 1 is the view showing the fabrication of the preferred embodiment according to the present disclosure; and FIG. 2 is the view showing the glass transition temperatures and the UL-94 grades of the phosphorus-containing epoxy thermoset.

DESCRIPTION OF THE PREFERRED EMBODIMENT

The following description of the preferred embodiment is provided to understand the features and the structures of the present disclosure.

Please refer to FIG. 1, which is a view showing fabrication of a preferred embodiment according to the present disclosure. As shown in the figure, the present disclosure is a process of synthesizing multi-functional phosphorus-containing epoxy curing agent, where cheap materials are obtained to fabricate a multi-functional phosphorous compound having good processability to be used as an epoxy resin curing agent. The present disclosure is a phosphorus compound or a phosphorus mixture and has the following formula (I):

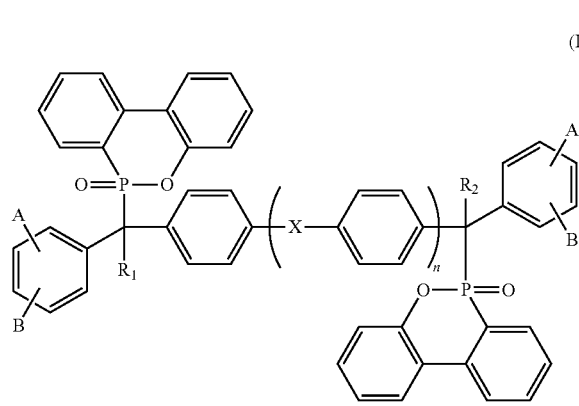

Therein, $R_1$ and $R_2$ are $C_1$~$C_6$ alkane, $C_3$~$C_6$ cycloalkane group, phenyl group or —$CF_3$; n is an integer selected from 0 to 10; A and B are —OH or —$NH_2$; X is a chemical group selected from a group consisting of null,

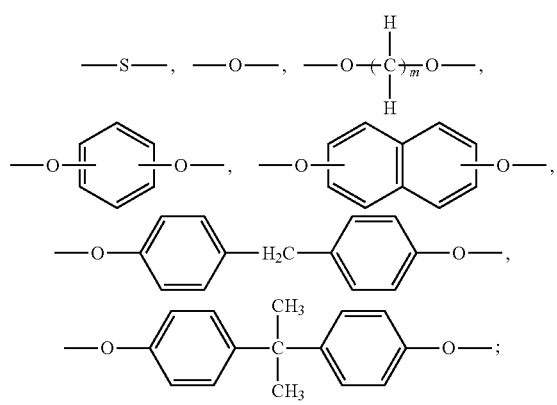

and, m is an integer selected from 1 to 10.

When $R_1$ and $R_2$ are methyl groups, n=1, X is a ether group and A and B are both —OH, the formula (I) is formula ($DMEP_4$):

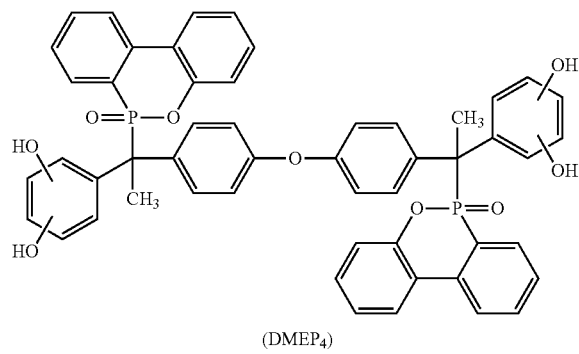

Therein, the formula ($DMEP_4$) can be formula (A) or formula (D):

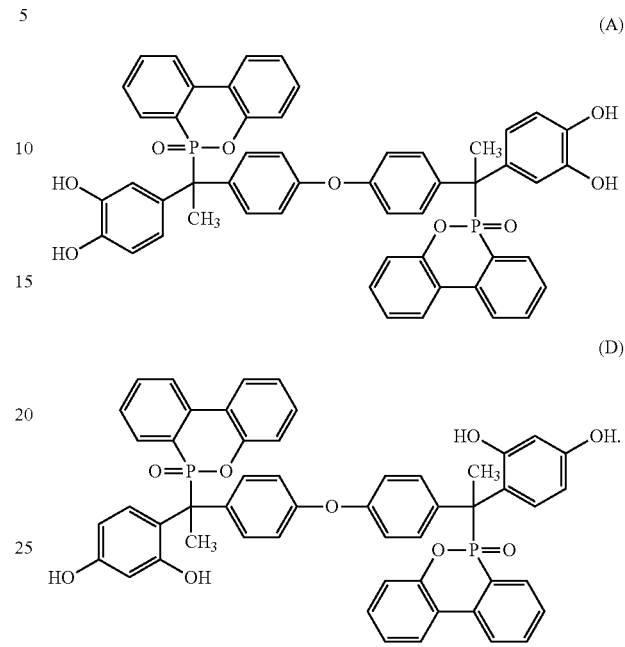

When $R_1$ and $R_2$ are methyl groups, n=1, X is a ether group and A and B are both —$NH_2$, the formula (I) is formula ($DMEA_4$):

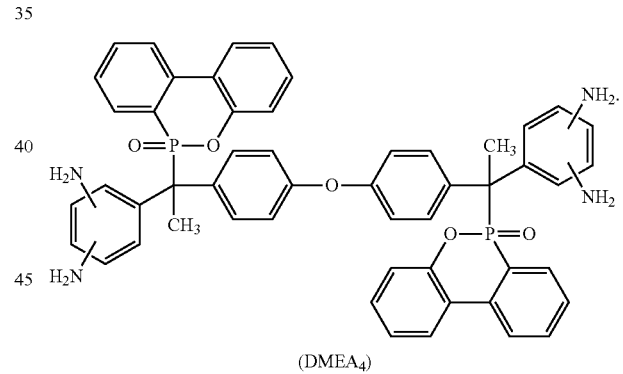

Therein, the formula ($DMEA_4$) can be formula (B) or formula (E):

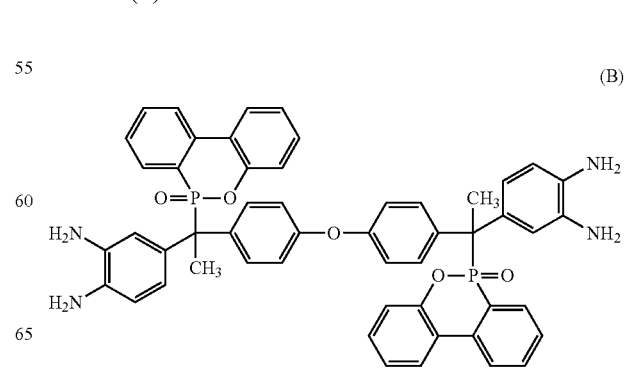

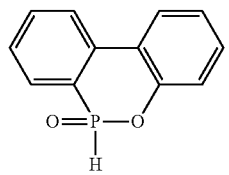

(II)

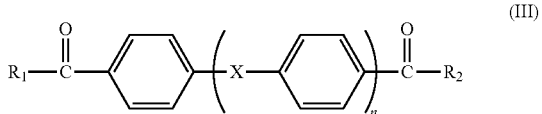

(III)

(IV)

where $R_1$, $R_2$, A, B, X and n are defined as the above.

When $R_1$ and $R_2$ are methyl groups, n=1, X is a ether group and A and B are both —OH, the formula (II) is 9,10-dihydro-9-oxa-10-phosphaphenanthrene-10-oxide (DOPO), the formula (III) is 4-acetylphenyl ether and the formula (IV) is catechol for reacting with the acid catalyst to obtain the curing agent having the formula (A). Or, the formula (II) is DOPO, the formula (III) is 4-acetylphenyl ether and the formula (IV) is resorcinol for reacting with the acid catalyst to obtain the curing agent having the formula (D).

When $R_1$ and $R_2$ are methyl groups, n=1, X is a ether group and A and B are both —$NH_2$, the formula (II) is DOPO, the formula (III) is 4-acetylphenyl ether and the formula (IV) is o-phenylenediamine for reacting with the acid catalyst to obtain the curing agent having the formula (B). Or, the formula (II) is DOPO, the formula (III) is 4-acetylphenyl ether and the formula (IV) is m-phenylenediamine for reacting with the acid catalyst to obtain the curing agent having the formula (E).

When $R_1$ and $R_2$ are methyl groups, n=1, X is a ether group and A and B are separately —OH and —$NH_2$, the formula (II) is DOPO, the formula (III) is 4-acetylphenyl ether and the formula (IV) is 2-aminophenol for reacting with the acid catalyst to obtain the curing agent having the formula (C). Or, the formula (II) is DOPO, the formula (III) is 4-acetylphenyl ether and the formula (IV) is 3-aminophenol for reacting with the acid catalyst to obtain the curing agent having the formula (F).

Thus, a phosphorus compound having reactive phenol and amine functional groups at end terminal is obtained to be used as an epoxy resin curing agent.

The acid catalyst is oxalic acid, p-toluenesulfonic acid (pTSA), acetic acid, methanesulfonic acid, trifluoromethane sulfonic acid, sulfuric acid, haloid acid (HX), trifluoroactic acid ($CF_3COOH$), nitric acid ($HNO_3$) or phosphoric acid ($H_3PO_4$).

The curing agent can be cured to obtain a phosphorus-containing epoxy thermoset with flame retardancy characteristic:

[State-of-Use 1] Obtaining Compound Having Formula (A)

The organic diphenyl phosphinate compound of DOPO, catechol, 4-acetylphenyl ether and the acid catalyst are used to obtain a phosphorus compound having formula (A), where n=1, X is a ether group, $R_1$ and $R_2$ are methyl groups and A and B are both —OH. The phosphorus compound having formula (A) is obtained through the following processes:

(E)

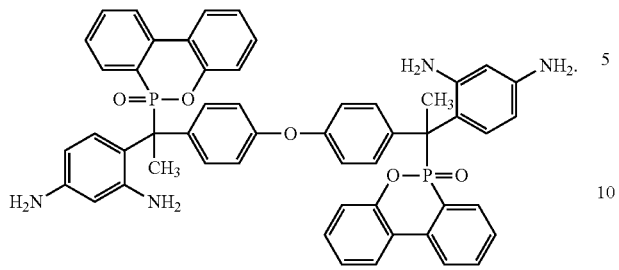

When $R_1$ and $R_2$ are methyl groups, n=1, X is a ether group and A and B are separately —OH and —$NH_2$, the formula (I) is formula ($DMEP_2A_2$):

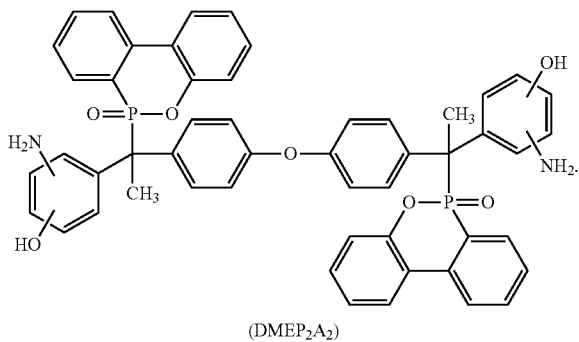

($DMEP_2A_2$)

Therein, the formula ($DMEP_2A_2$) can be formula (C) or formula (F):

(C)

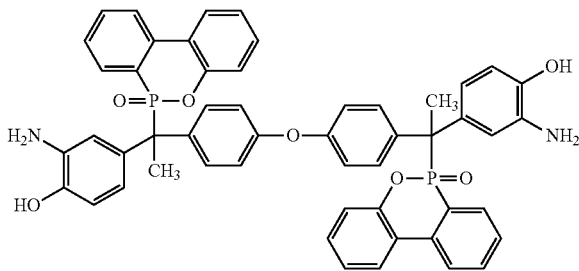

(F)

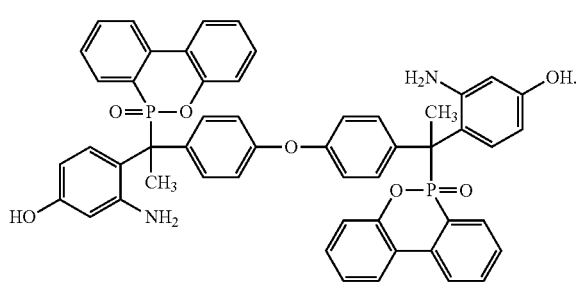

The present disclosure has a fabrication method, including obtaining organic phosphorous compounds having formula (II), formula (III) and formula (IV) to be reacted with an acid catalyst to obtain the curing agent having said formula (I):

2.16 grams (g) (0.01 mole (M)) of organic diphenyl phosphinate compound of DOPO, 5.5 g (0.05M) of catechol, 1.27 g (0.005M) of 4-acetylphenyl ether and 0.086 g (4 wt % of DOPO) of p-toluenesulfinic acid are obtained to be put into a 100 milliliter (ml) three-necked round-bottom flask. Then, the temperature is increased to 90 Celsius degrees (° C.) to be maintained for reaction for 24 hours (hr) with stirring. Then, the stirring is stopped and the flask is cooled down to a room temperature. A small amount of ethanol solution is added and 1:1 of water/methanol is dropped for filtration. After being hot-dried, a brown-powdered product having formula (A) is obtained with a yield about 84%, which can be re-crystallized with ethanol/water: HR-MS (FAB+) m/z: calcd. for $C_{52}H_{40}O_9P_2$ 870.2148; anal., 870.2158, for $C_{52}H_{40}O_9P_2$.

[State-of-Use 2] Obtaining Compound Having Formula (B)

The organic diphenyl phosphinate compound of DOPO, catechol, 4-acetylphenyl ether and the acid catalyst are used to obtain a phosphorus compound having formula (B), where n=1, X is a ether group, $R_1$ and $R_2$ are methyl groups and A and B are both —$NH_2$. The phosphorus compound having formula (B) is obtained through the following processes:

2.16 g (0.01 M) of organic diphenyl phosphinate compound of DOPO, 5.41 g (0.05M) of catechol, 1.27 g (0.005M) of 4-acetylphenyl ether and 0.086 g (4 wt % of DOPO) of p-toluenesulfinic acid are obtained to be put into a 100 ml three-necked round-bottom flask. Then, the temperature is increased to 130° C. to be maintained for reaction for 24 hrs with stirring. Then, the stirring is stopped and the flask is cooled down to a room temperature. A small amount of ethanol solution is added and water is dropped for filtration. After being hot-dried, a purple-powdered product having formula (B) is obtained with a yield about 81%: HR-MS (FAB+) m/z: calcd. for $C_{52}H_{44}N_2O_5P_4$ 866.2787; anal., 866.2742, C52, H44, N2, O5, P4.

[State-of-Use 3] Obtaining Compound Having Formula (C)

The organic diphenyl phosphinate compound of DOPO, 2-aminophenol, 4-acetylphenyl ether and the acid catalyst are used to obtain a phosphorus compound having formula (C), where n=1, X is a ether group, $R_1$ and $R_2$ are methyl groups and A and B are separately —OH and —$NH_2$. The phosphorus compound having formula (C) is obtained through the following processes:

2.16 g (0.01 M) of organic diphenyl phosphinate compound of DOPO, 5.45 g (0.05M) of 2-aminophenol, 1.27 g (0.005M) of 4-acetylphenyl ether, 0.086 g (4 wt % of DOPO) of trifluoromethane sulfonic acid and 5 ml of dimethyl sulfoxide (DMSO) are obtained to be put into a 100 ml three-necked round-bottom flask. Then, the temperature is increased to 60° C. to be maintained for reaction for 24 hrs with stirring. Then, the stirring is stopped and the flask is cooled down to a room temperature. Water is dropped for filtration and 1:1 of water/methanol is used for washing several times. After being hot-dried, a product having formula (C) is obtained with a yield about 72%: HR-MS (FAB+) m/z: calcd. for $C_{52}H_{42}N_2O_7P_2$ 868.2467; anal., 868.2455, C52, H42, N2, O7, P2.

[State-of-Use 4] Obtaining Compound Having Formula (D)

The organic diphenyl phosphinate compound of DOPO, resorcinol, 4-acetylphenyl ether and the acid catalyst are used to obtain a phosphorus compound having formula (D), where n=1, X is a ether group, $R_1$ and $R_2$ are methyl groups and A and B are both —OH. The phosphorus compound having formula (D) is obtained through the following processes:

2.16 g (0.01 M) of organic diphenyl phosphinate compound of DOPO, 5.5 g (0.05M) of resorcinol, 1.27 g (0.005M) of 4-acetylphenyl ether and 0.086 g (4 wt % of DOPO) of p-toluenesulfinic acid are obtained to be put into a 100 ml three-necked round-bottom flask. Then, the temperature is increased to 90° C. to be maintained for reaction for 24 hrs with stirring. Then, the stirring is stopped and the flask is cooled down to a room temperature. A small amount of ethanol solution is added and 1:1 of water/methanol is dropped for filtration. After being hot-dried, a yellow-powdered product having formula (D) is obtained with a yield about 78%: HR-MS (FAB+) m/z: calcd. for $C_{52}H_{40}O_9P_2$ 870.2148; anal., 870.2158, C52, H40, O9, P2.

[State-of-Use 5] Obtaining Compound Having Formula (E)

The organic diphenyl phosphinate compound of DOPO, m-phenylenediamine, 4-acetylphenyl ether and the acid catalyst are used to obtain a phosphorus compound having formula (E), where n=1, X is a ether group, $R_1$ and $R_2$ are methyl groups and A and B are both —$NH_2$. The phosphorus compound having formula (E) is obtained through the following processes:

2.16 g (0.01 M) of organic diphenyl phosphinate compound of DOPO, 5.41 g (0.05M) of m-phenylenediamine, 1.27 g (0.005M) of 4-acetylphenyl ether and 0.086 g (4 wt % of DOPO) of p-toluenesulfinic acid are obtained to be put into a 100 ml three-necked round-bottom flask. Then, the temperature is increased to 130° C. to be maintained for reaction for 24 hrs with stirring. Then, the stirring is stopped and the flask is cooled down to a room temperature. A small amount of ethanol solution is added and water is dropped for filtration. After being hot-dried, a brown-powdered product having formula (E) is obtained with a yield about 75%: HR-MS (FAB+) m/z: calcd. for $C_{52}H_{44}N_2O_5P_4$ 866.2787; anal., 866.2742, C52, H44, N2, O5, P4.

[State-of-Use 6] Obtaining Compound Having Formula (F)

The organic diphenyl phosphinate compound of DOPO, 3-aminophenol, 4-acetylphenyl ether and the acid catalyst are used to obtain a phosphorus compound having formula (F), where n=1, X is a ether group, $R_1$ and $R_2$ are methyl groups and A and B are separately —OH and —$NH_2$. The phosphorus compound having formula (F) is obtained through the following processes:

2.16 g (0.01 M) of organic diphenyl phosphinate compound of DOPO, 5.45 g (0.05M) of 3-aminophenol, 1.27 g (0.005M) of 4-acetylphenyl ether and 0.086 g (4 wt % of DOPO) of trifluoromethane sulfonic acid are obtained to be put into a 100 ml three-necked round-bottom flask. Then, the temperature is increased to 90° C. to be maintained for reaction for 24 hrs with stirring. Then, the stirring is stopped and the flask is cooled down to a room temperature. A small amount of ethanol solution is added and water is dropped for filtration. After being hot-dried, a brown-powdered product having formula (F) is obtained with a yield about 78%: HR-MS (FAB+) m/z: calcd. for $C_{52}H_{42}N_2O_7P_2$ 868.2467; anal., 868.2455, C52, H42, N2, O7, P2.

[State-of-Use 7] Obtaining Phosphorus-Containing Epoxy Thermoset with Flame Retardancy Characteristic The compounds obtained in the state-of-use 1~3 are added in epoxy resindiglycidyl ether of bisphenol A (DGEBA) coordinated with a hardener of diaminodiphenyl sulfone (DDS) to be cured, where the reactant compositions with different phosphorus content are mixed in a 1:1 equivalent ratio. Then the temperature is increased to 150° C. to be molten. After being stirred for evenness, curing is processed with an oven at 180° C. for 2 hrs, 200° C. for 2 hrs and 220° C. for 2 hrs. Therein, the hardener can be phenol novolac, dicyandiamide, diaminodiphenyl methane, phthalic anhydride or hexahydrophthalic anhydride.

Please refer to FIG. 2, which is a view showing glass transition temperatures (Tg) and UL-94 grades of the phosphorus-containing epoxy thermoset. As shown in the figure, a phosphorus-containing epoxy thermoset obtained by curing the present disclosure has a high Tg when its thermo-tolerance effect reaches UL-94 V-0 grade. When a DAS-1.0 curing system reaches UL-94 V-0, its Tg is 214° C.; when a DBS-1.0 curing system reaches UL-94 V-0, its Tg is 224° C.; and, when a DCS-1.0 curing system reaches UL-94 V-0, its Tg is 219° C. Hence, the phosphorus-containing epoxy thermoset is fit for high Tg circuit board substrate, semiconductor packaging material and related materials.

To sum up, the present disclosure is a processes of synthesizing multi-functional phosphorus-containing epoxy curing agent, where cheap materials are obtained to fabricate a multi-functional phosphorous compound having good processability to be used as an epoxy resin curing agent; and where the curing agent can be further cured to be fit for high Tg circuit board substrate, semiconductor packaging material and related materials.

The preferred embodiments herein disclosed are not intended to unnecessarily limit the scope of the disclosure. Therefore, simple modifications or variations belonging to the equivalent of the scope of the claims and the instructions disclosed herein for a patent are all within the scope of the present disclosure.

What is claimed is:

1. A multi-functional phosphorus-containing epoxy curing agent,
   wherein said curing agent is selected from a group consisting of a phosphorus compound and a phosphorus mixture;
   wherein said curing agent has the following formula (I):

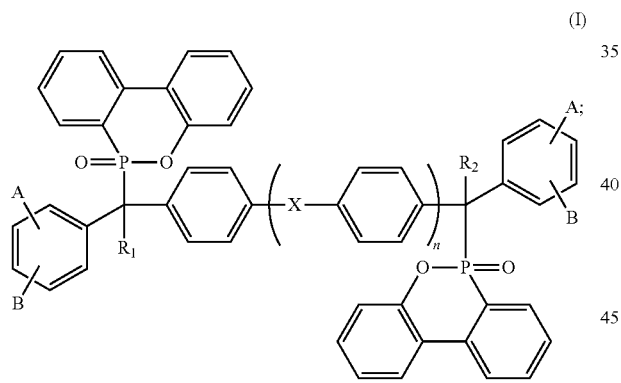

(I)

wherein each of $R_1$ and $R_2$ is selected from a group consisting of $C_1$~$C_6$ alkane, $C_3$~$C_6$ alkanecycloalkane group, phenyl group and —$CF_3$;
   wherein n is an integer selected from 0 to 10;
   wherein each of A and B is selected from a group consisting of —OH and —$NH_2$;
   wherein X is a chemical group selected from a group consisting of null,

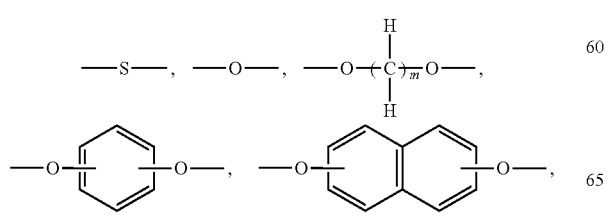

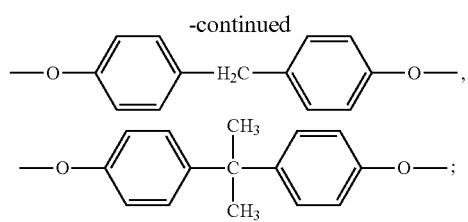

and
wherein m is an integer selected from 1 to 10.

2. The curing agent according to claim 1,
   wherein n=1, X is a ether group, $R_1$ and $R_2$ are methyl groups, A and B are both —OH and said formula (I) is formula ($DMEP_4$):

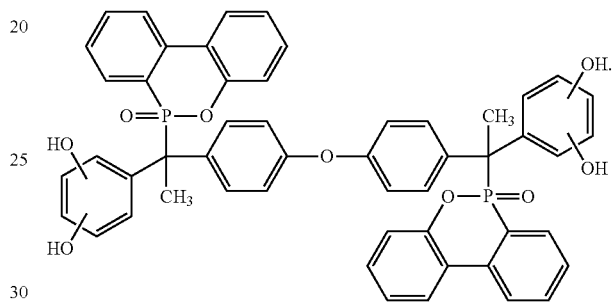

($DMEP_4$)

3. The curing agent according to claim 2,
   wherein said formula ($DMEP_4$) is a formula selected from a group consisting of formula (A) and formula (D):

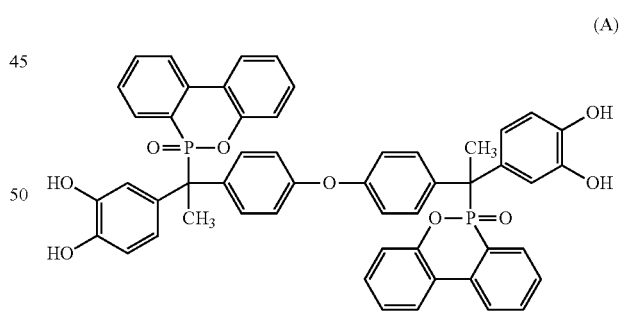

(A)

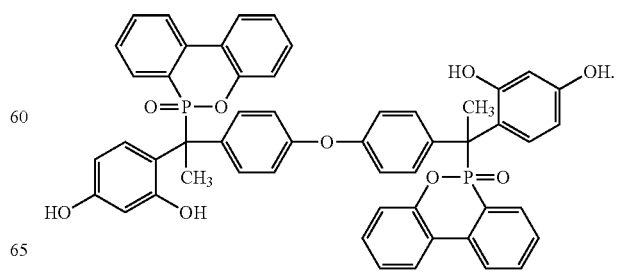

(D)

4. The curing agent according to claim 1,
wherein n=1, X is a ether group, $R_1$ and $R_2$ are methyl groups, A and B are both —$NH_2$ and said formula (I) is formula ($DMEP_4$).

5. The curing agent according to claim 4,
wherein said formula ($DMEP_4$) is a formula selected from a group consisting of formula (A) and formula (D):

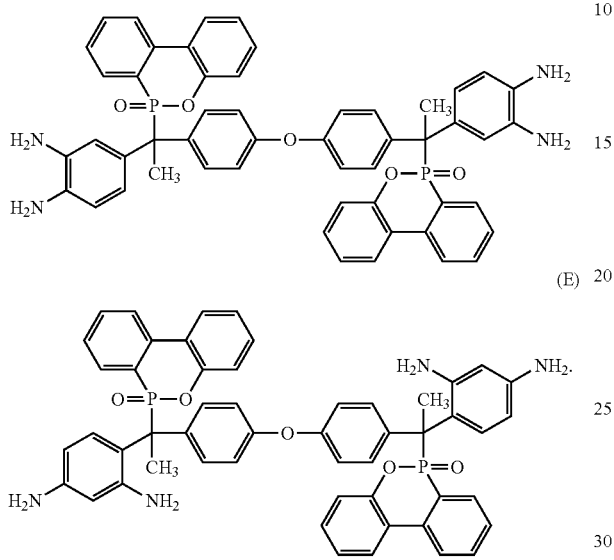

(B)

(E)

6. The curing agent according to claim 1,
wherein n=1, X is a ether group, $R_1$ and $R_2$ are methyl groups, A and B are separately —OH and —$NH_2$ and said formula (I) is formula ($DMEP_2A_2$):

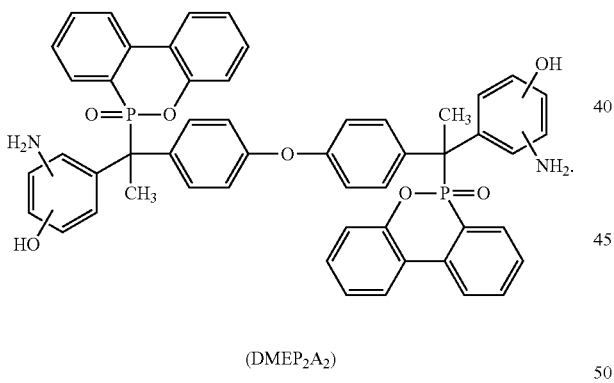

($DMEP_2A_2$)

7. The curing agent according to claim 2,
wherein said formula ($DMEP_4$) is a formula selected from a group consisting of formula (A) and formula (D):

(A)

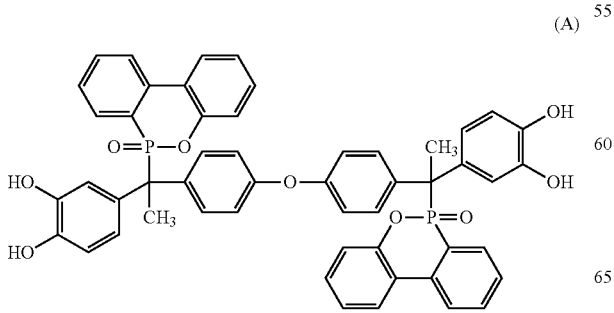

-continued (D)

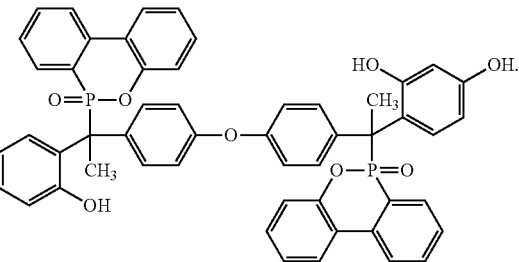

8. The curing agent according to claim 1,
wherein said curing agent has a fabrication method, including obtaining compounds to be reacted with an acid catalyst to obtain said curing agent having said formula (I);

wherein said compounds are organic phosphorous compounds having formula (II), formula (III) and formula (IV):

(II)

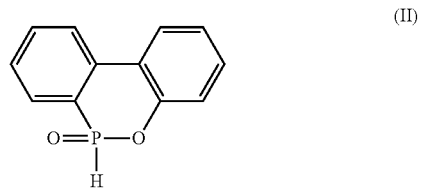

(III)

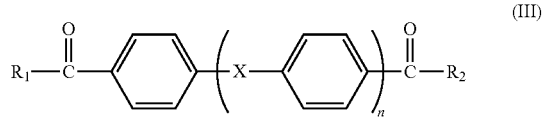

(IV)

wherein each of $R_1$ and $R_2$ is selected from a group consisting of $C_1$~$C_6$ alkane, $C_3$~$C_6$ alkanecycloalkane group, phenyl group and —$CF_3$;

wherein n is an integer selected from 0 to 10;

wherein each of A and B is selected from a group consisting of —OH and —$NH_2$;

wherein X is a chemical group selected from a group consisting of null,

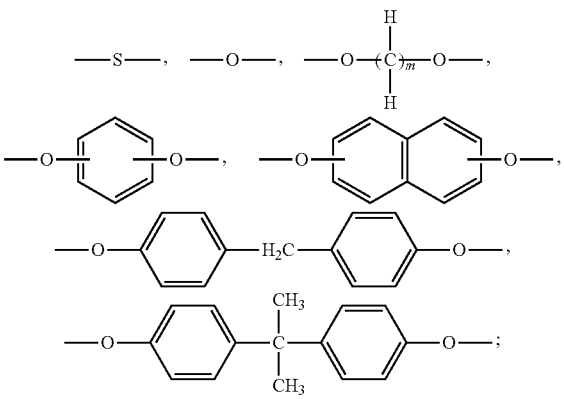

and wherein m is an integer selected from 1 to 10.

9. The curing agent according to claim 8,
wherein n=1, X is a ether group, $R_1$ and $R_2$ are methyl groups, A and B are both —OH and said formula (I), said formula (II), said formula (III) and said formula (IV) are:

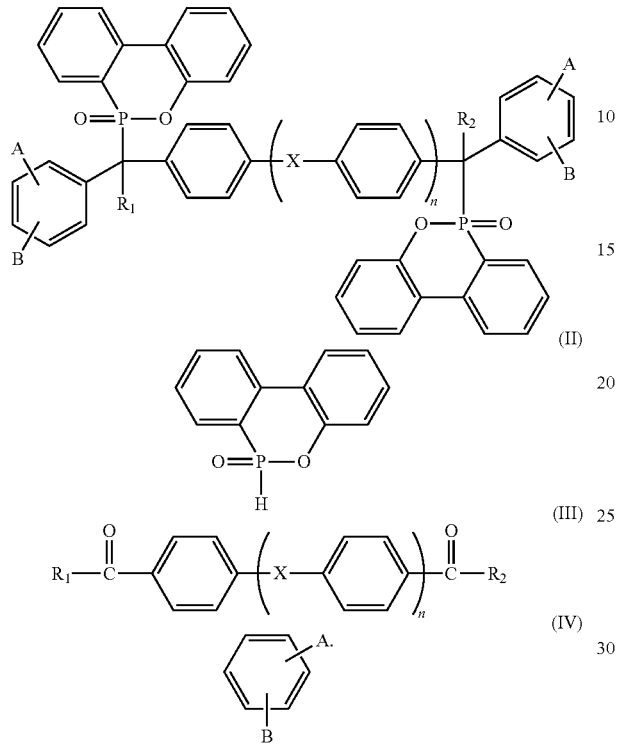

10. The curing agent according to claim 9,
wherein said formula (II) is 9,10-dihydro-9-oxa-10-phosphaphenanthrene 10-oxide (DOPO), said formula (III) is 4-acetylphenyl ether, said formula (IV) is catechol and said formula (I) is formula (A):

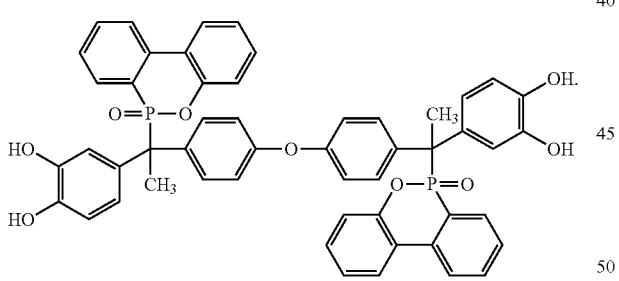

11. The curing agent according to claim 9,
wherein said formula (II) is DOPO, said formula (III) is 4-acetylphenyl ether, said formula (IV) is resorcinol and said formula (I) is formula (D):

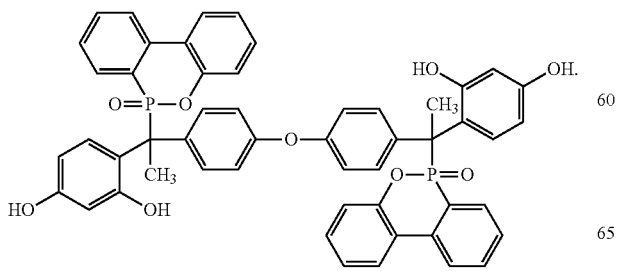

12. The curing agent according to claim 8,
wherein n=1, X is a ether group, $R_1$ and $R_2$ are methyl groups, A and B are both —$NH_2$ and said formula (I), said formula (II), said formula (III) and said formula (IV) are:

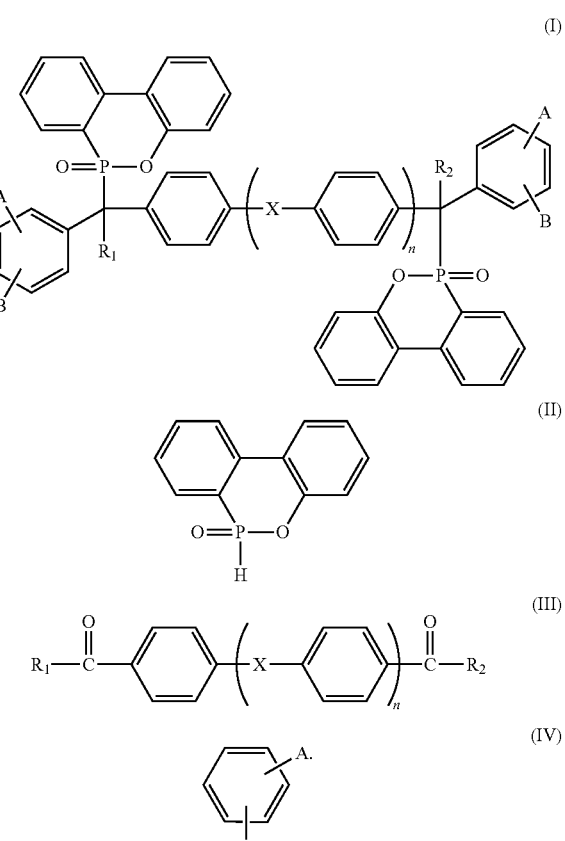

13. The curing agent according to claim 12,
wherein said formula (II) is DOPO, said formula (III) is 4-acetylphenyl ether, said formula (IV) is o-phenylenediamine and said formula (I) is formula (B):

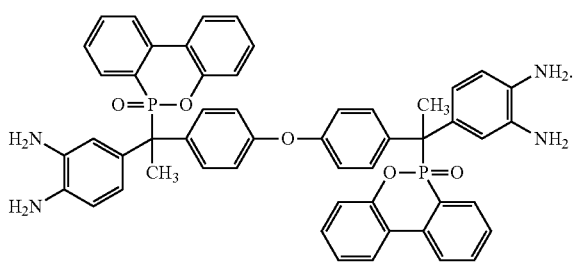

14. The curing agent according to claim 12,
wherein said formula (II) is DOPO, said formula (III) is 4-acetylphenyl ether, said formula (IV) is m-phenylenediamine and said formula (I) is formula (E):

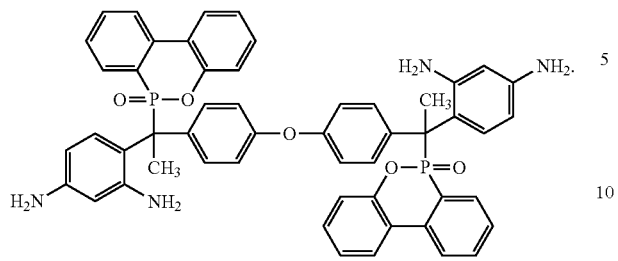

15. The curing agent according to claim 8,
wherein n=1, X is a ether group, $R_1$ and $R_2$ are methyl groups, A and B are separately —OH and —$NH_2$ and said formula (I), said formula (II), said formula (III) and said formula (IV) are:

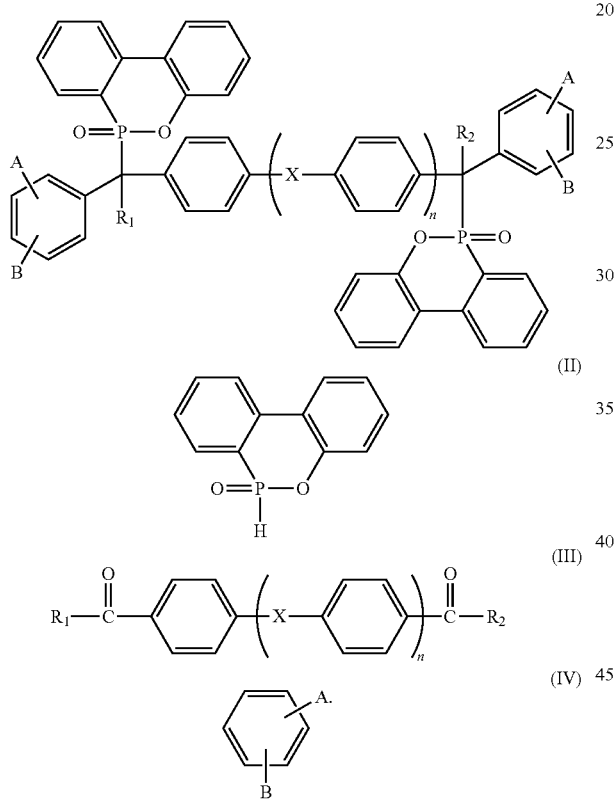

16. The curing agent according to claim 15,
wherein said formula (II) is DOPO, said formula (III) is 4-acetylphenyl ether, said formula (IV) is 2-aminophenol and said formula (I) is formula (C):

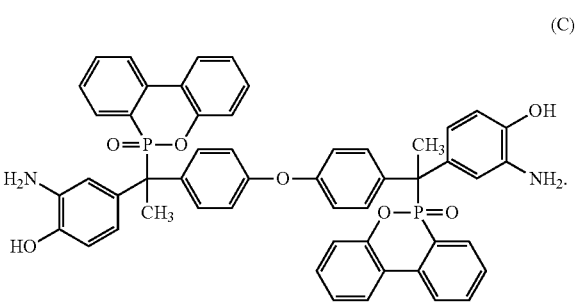 [SMILES: CC(c1ccc(Oc2ccc(C(C)(c3ccc(O)c(N)c3)P3(=O)Oc4ccccc4-c4ccccc43)cc2)cc1)(c1ccc(O)c(N)c1)P1(=O)Oc2ccccc2-c2ccccc21]

17. The curing agent according to claim 15,
wherein said formula (II) is DOPO, said formula (III) is 4-acetylphenyl ether, said formula (IV) is 3-aminophenol and said formula (I) is formula (F):

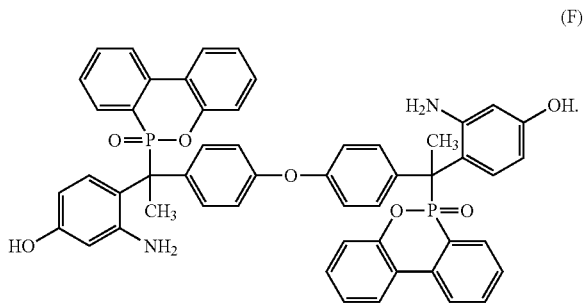 [SMILES: CC(c1ccc(Oc2ccc(C(C)(c3ccc(O)cc3N)P3(=O)Oc4ccccc4-c4ccccc43)cc2)cc1)(c1ccc(O)cc1N)P1(=O)Oc2ccccc2-c2ccccc21]

18. The curing agent according to claim 8,
wherein said acid catalyst is selected from a group consisting of oxalic acid, p-toluenesulfonic acid (pTSA), methanesulfonic acid, trifluoromethane sulfonic acid, sulfuric acid, haloid acid (HX), trifluoroactic Acid ($CF_3COOH$), nitric acid ($HNO_3$), and phosphoric acid ($H_3PO_4$).

* * * * *